United States Patent [19]

Graham et al.

[11] Patent Number: 4,973,304
[45] Date of Patent: Nov. 27, 1990

[54] DEVICE FOR SUSTAINED RELEASE OF ACTIVE SUBSTANCE

[75] Inventors: Neil B. Graham, Bearsden; Ernst R. Huehns, London; Marion E. McNeill, Milngavie, all of United Kingdom

[73] Assignee: National Research Development Corporation, London, England

[21] Appl. No.: 477,128

[22] Filed: Feb. 7, 1990

Related U.S. Application Data

[63] Continuation of Ser. No. 231,583, Aug. 8, 1988, abandoned, which is a continuation of Ser. No. 45,215, Apr. 3, 1987, abandoned, which is a continuation of Ser. No. 851,279, Apr. 10, 1986, abandoned, which is a continuation of Ser. No. 669,129, Jan. 7, 1985, abandoned.

[30] Foreign Application Priority Data

Feb. 7, 1984 [GB] United Kingdom ............... 8403138

[51] Int. Cl.⁵ .............................................. A61M 31/00
[52] U.S. Cl. ................................. 604/48; 604/49; 604/55; 424/424
[58] Field of Search .................. 604/48, 49, 55; 424/423, 424

[56] References Cited

U.S. PATENT DOCUMENTS

| 3,093,831 | 6/1963 | Jordan | 623/60 |
| 3,796,217 | 3/1974 | Arien | |
| 3,896,806 | 7/1975 | Wichterle | 623/66 |
| 3,946,734 | 3/1976 | Dedrick et al. | 604/49 X |
| 3,971,376 | 7/1976 | Wichterle | 604/49 X |
| 4,220,153 | 9/1980 | Dresback | 604/892 X |
| 4,814,182 | 3/1989 | Graham et al. | |

OTHER PUBLICATIONS

*Hacth's Chemical Dictionary*, 4th Ed., McGraw-Hill, Inc., 1969, pp. 293,332.
132,384, European Patent Application, published July 30, 1985.

*Primary Examiner*—Alan W. Cannon
*Attorney, Agent, or Firm*—Oblon, Spivak, McClelland, Maier & Neustadt

[57] ABSTRACT

A device for the sustained release of active substance comprises a wall defining a cavity for the reception of active substance, the wall being of impermeable material and having one or more ports therethrough. Sections of hydrogel material are within the cavity, the hydrogel, in use, being swollen to cover the ports in the cavity wall. Active ingredient is released from the container only through the hydrogel covering the ports. In this way sustained and controlled release of the active substance from the device is obtained.

14 Claims, 3 Drawing Sheets

DEVICE FOR SUSTAINED RELEASE OF ACTIVE SUBSTANCE

This application is a continuation of application Ser. No. 07/045,215, filed Apr. 3, 1987, which is a continuation of Ser. No. 06/851,279, filed on Apr. 10, 1986, which is a continuation of Ser. No. 06/669,129, filed on Jan. 7, 1985, now abandoned.

This invention relates to a device for the sustained release of active substance.

There are many applications, particularly in the medical and veterinary fields, where the sustained release of active substance is desirable. For some conditions it is known to provide pharmaceuticals in a slow release, for example capsule or tablet, form. The patient swallows the necessary capsules or tablets and then the pharmaceutical is released slowly in the patient's digestive tract. While this method of treatment has a high level of patient acceptability, it is unfortunately not one which is available for all treatments where sustained release is desired.

For example, in patients suffering from incurable severe anemia, for example, thalassaemia major, life can be maintained by regular blood transfusion. This inevitably leads to iron overload which causes liver disease, endocrine failure and cardiac abnormalities, eventually leading to death after a number of years. Preventative treatment comprises regular daily subcutaneous infusion of desferrioxamine over a period of 12 hours. However, even with modern techniques, such treatment is arduous and patient compliance is poor.

Many diabetics have to inject themselves with comparatively large doses of insulin once or twice a day. This results in large fluctuations in blood sugar/insulin levels between injections. Recent studies have shown that sustained administration of lower amounts of insulin over longer periods is a preferable treatment method to maintain more constant levels within the body.

According to the present invention there is provided a sustained release device for releasing active substance from a cavity containing the active substance through a layer of hydrogel covering at least one port in a wall made of water-impermeable material, wherein the wall defines the cavity for the reception of active substance and the cavity contains at least one body of hydrogel material which hydrogel material when in swollen condition is not contiguous with the entire cavity wall but covers the port or ports in the wall.

In use of the device according to the invention, the hydrogel material is maintained in swollen condition so that it covers the port or ports in the cavity wall. This may for example be achieved by having the active substance within the cavity in an aqueous medium and/or by using the device in an aqueous environment. This ensures that the hydrogel is kept in hydrated state and thus swollen.

Active substance, e.g. in aqueous solution or suspension, is provided within the cavity of the device according to the invention.

The active substance is in use released from the device according to the invention only by diffusion through the swollen hydrogel layer formed across the ports in the cavity wall and thus out into its surroundings. By choice of materials and the number and size of the ports in the cavity walls for example, the rate of release of active substance from the device according to the invention can be controlled very accurately making the device particularly suitable for medical and veterinary use and any other use where accurate administration rates are important. Moreover, the water-impermeable walls can be robust. Thus the invention provides a device having a robustness in use and control of release of active substance provided by the hydrogel. Preferably the walls are of flexible material.

A particularly interesting application of the devices according to the invention in medical or veterinary use is their use as implants or as inserts. Thus the devices according to the invention can be implanted surgically into the body or introduced into a body cavity of a human patient or an animal such that the active substance diffuses out of the device through the hydrogel windows into the surrounding body region.

Especially when the device is to be used as a surgical implant it is desirable that the device should be rechargeable in situ. Thus the device may comprise at least one, preferably two, releasable seals whereby active substance can be introduced and/or replenished when the device is implanted. The releasable seals, which can be for example a rubber cap, valve or nipple, are then provided to the exterior of the patient when the device is implanted. Alternatively the device walls may be of a self-sealing material so that access to the cavity for replenishment of active ingredient can then be achieved by a hypodermic. This self-sealing device may in particular be used as a subcutaneous implant and then the cavity of the device replenished by injection through the skin and walls therebelow.

It is important, when the device according to the invention is to be replenished by hypodermic, that the hypodermic be introduced through the cavity wall material only (not through the hydrogel material) since the hydrogel tends to be fractured and thus will deteriorate if punctured by a needle. Thus there should be a substantial proportion of cavity wall with which the hydrogel has no contact. Indeed it is in all embodiments preferred that the walls are of flexible material with the swollen hydrogel being in contact with the cavity walls substantially only in the region of the ports. In this way the device is a flexible robust structure in contrast to the weaker nick sensitive properties of hydrogel alone.

Most conveniently the device according to the present invention is in the form of a tube of water-impermeable material having at least one port in the tube wall. Preferably the tube wall will have a plurality of ports along its length. The tube will then contain at least one annular section of hydrogel material which when in swollen condition extends across the port or ports in the tube wall.

For production of the device according to the invention the hydrogel material can be positioned in the cavity when it is in the dry state. For use the hydrogel is hydrated to cause it to swell and to contact with the cavity wall in the region of the ports to form a layer across the ports. The hydrogel can be hydrated before introduction of the active substance. However if the active substance is in an aqueous medium then that water present can be used to hydrate the hydrogel.

During use the hydrogel must be maintained in the swollen state. If the active substance is in aqueous medium then this will ensure that the hydrogel is always hydrated. If the active substance is in a non-aqueous medium, the hydrated state of the hydrogel may be maintained if the device is provided in an aqueous environment, e.g. surrounded by body fluids.

As mentioned above, one particularly interesting use of the device according to the present invention is as a rechargeable implant device. Thus a tube according to the present invention can be implanted surgically within a patient, each end of the tube being connected to the outside of the patient, where it is provided with a rubber cap, valve, nipple or other suitable sealing device. Active substance solution for example can then be introduced into the implanted device through, e.g. caps provided to the exterior of the patient. The active substance introduced in this way then diffuses out through the hydrogel layers across the ports in the tube wall into the surrounding patient body region.

When desired, for example when the active substance previously introduced has been exhausted, the implanted device according to the present invention can be replenished in situ by introduction of further active substance solution into the device through the caps provided to the exterior of the patient. In this way the patient can be provided with controlled amounts of active substance over long periods of time in a manner much more acceptable to the patient than other methods previously used. In the event that it should for any reason become desirable, e.g. due the introduction of any infection, the implanted device of the present invention can be flushed out, again in situ, before replenishment with the active substance solution.

Alternatively where e.g. having caps to the exterior of a patient is unacceptable, a self-sealing device according to the present invention can be implanted subcutaneously. Such a device can for example be toroidal being formed by the joining together of the ends of the tube device according to the invention. When the device requires replenishment this can be done in situ by introducing active substance solution through the skin and device wall using a hypodermic needle.

In thalassaemia therapy, a device according to the present invention can be implanted subcutaneously in the peritoneal region or can be implanted directly into the peritoneal cavity. Desferrioxamine, in isotonic solution, is introduced into the implanted device through the for example caps to the exterior of the patient's body. This desferrioxamine will then diffuse, over a prolonged period of time, into the patient's peritoneum. Thus with the device according to the present invention desferrioxamine solution has only to be introduced intermittently into the implanted device and thus is more patient acceptable than the present continuous infusion method but still enables desferrioxamine to enter the peritoneal cavity on a continuous basis. Indeed with the device according to the present invention desferrioxamine can be introduced gradually over 24 hours per day whereas with the present infusion method only 12 hours infusion has been found at all acceptable to patients.

Similarly, the device according to the present invention can be used for the treatment of diabetics. Thus the device can be surgically implanted and used for the administration of insulin to the diabetic. The insulin has only to be introduced into the device according to the present invention e.g. once or twice a day as at present but with the device according to the present invention the insulin will then be released into the patient's body over a prolonged period of time. Thus blood sugar/insulin levels within the diabetic can be kept more constant than with the conventional injection method.

In a similar way, the device according to the present invention can be inserted into animals where sustained release, e.g. of hormones, into the animal is desired.

For many applications the most convenient treatment is provided by surgically implanting a device according to the present invention. However this is not always necessary. For example the device according to the present invention, e.g. toroidal in shape, may be introduced into a body cavity, e.g. into the vagina around the cervix. In this embodiment the device according to the present invention may contain a contraceptive such a laevo-norgestrel, or a spermicide, such as nonoxynolphenol, for local action or other active material for systemic absorption across the vagina wall membrane, which will be released, by diffusion through the hydrogel layers of the device. In this embodiment of the invention, when exhausted, the device is removed from the body cavity and then either replenished and replaced or a new, fully charged device, can be inserted.

The rate of release of active substance from the device according to the present invention depends on several factors. Thus it depends upon the diffusion rate of active substance through the hydrogel layer material, the type of hydrogel itself and the thickness of the hydrogel layer and the concentration of active substance as well as upon the total area of perforations through the cavity wall and the number and size of those perforations. The rate of release of active substance is not necessarily directly proportional to the total area, number and size of the ports in the wall of the device according to the present invention as other factors concerning the environment of the device in use may also affect this. However the dependency of the rate of release on the total area, number and size of the perforations can readily be determined. It will thus be seen that by a suitable choice of the characteristics, very accurate and controlled release rates of active substance from the device according to the present invention can be achieved.

For medical use, the active substance in the device according to the present invention will normally be in aqueous, isotonic, solution and, under these conditions, the water present will cause the hydrogel to swell and maintain the hydrogel in swollen condition. However the device can also be used with drugs in non-aqueous media e.g. in biocompatible oils such as olive oil, peanut oil. In these circumstances the hydrogel is hydrated before insertion and then the water present in the body fluids will generally be sufficient to maintain hydration of the hydrogel and thus the seal of the hydrogel to the cavity walls.

For prolonged constant release of active substance it is preferred that the active substance in the device according to the invention be in saturated solution, suitably with some active substance in suspension in the saturated solution. Thus as active substance is lost from the device, suspended material enters into saturated solution.

As explained above the device according to the invention may be used for the sustained release of desferrioxamine, insulin and contraceptives and spermicides. Also the device could be used for cancer therapy drugs using e.g. steroids and for the delivery of peptides and prostanoids. The device can be further used e.g. for the introduction of hormones into animals.

In addition of course the device according to the present invention can be used in the non-medical and non-veterinary fields where introduction of active substance to an aqueous environment is desired.

The device according to the present invention can be of any suitable material. The water-impervious material of the wall of the device according to the present invention provides the device with the necessary mechanical strength which hydrogel materials by themselves do not normally have. The wall is preferably of elastomeric material so that the overall device is flexible for ease of handling. Naturally, for medical use, the device must be of a medical grade material. Thus, for medical use, there is preferably used, as wall material, medical grade silicon rubber tubing though other hydrophobic elastomers are also suitable.

The hydrogel used may be selected from any of appropriate mechanical or chemical stability, for example there may be used polyacrylamides, poly-N-vinyl pyrrolidones, polyhydroxyethyl and -propyl (meth)acrylates and polyethoxylated derivatives thereof, crosslinked polyvinyl alcohols and crosslinked starches, dextrans, polyhydric natural products, polyacrylic and methacrylic acids, crosslinked proteins, e.g. crosslinked collagen and crosslinked glutamic aid. The hydrogel material used must of course be one through which the active substance proposed to be used can diffuse.

There may be used as hydrogel a crosslinked poly-(ethylene glycol or ethylene oxide). Suitable crosslinked materials can be prepared by reacting for example molar equivalents of poly(ethylene oxide) or poly(ethylene glycol) with difunctional isocyanates e.g. 4,4'-diphenylmethane diisocyanate or its fully hydrogenated equivalent 4,4'-cyclo-hexylmethane diisocyanate combined with a polyol such as e.g. trimethylolpropane, 1,2,6-hexantriol or low molecular weight oxypropylated or oxyethylated polyols commonly available for the manufacture of rigid polyurethane foams. Alternatively there may be used the crosslinked products of di- or tri- functional poly(ethylene glycol) and tri-or more fuctional isocyanates e.g. the crude diphenylmethane diisocyanate as sold by I.C.I. under the Trade Mark SUPRASEC.

The hydrogel is preferably introduced into the device in accordance with the present invention in the form of e.g. annular cylindrical sections which, after introduction and hydration, swell up against the inside cavity walls. The hydrogel bodies can be formed on polymerisation, by drilling of blocks of hydrogel material to provide the necessary annular shape or they may be formed by polymerising or depositing polymer layers on a mandrel or by other conventional techniques used in the plastics industry.

The invention also provides a sustained release device according to the invention having in the cavity Thereof active substance. Preferably the active substance is present in the device in saturated solution or is present in such amount that on introduction of aqueous medium into the device saturated solution is formed.

The invention further provides a method of administering active substance to a patient which method comprises implanting into or introducing into the patient's body a device according to the invention containing active substance and maintaining the hydrogel in swollen condition.

The invention is further illustrated by way of example with reference to the accompanying drawings wherein.

Figure 1:
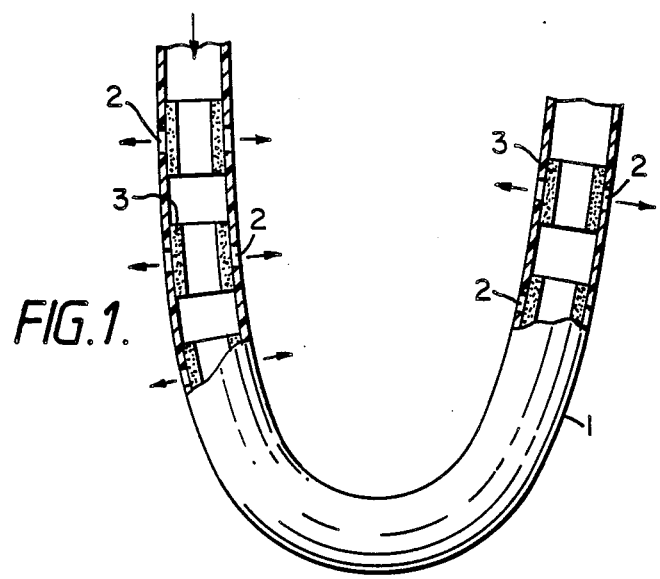
FIG. 1 is a part section through an implant device according to the present invention.

Referring to FIG. 1, there is shown a tube 1 of water-impermeable material, e.g. medical grade silicon rubber. Within the walls of tube 1 are a plurality of ports 2. Inside the tube 1 are a plurality of annular cylindrical sections 3 of hydrogel material. Each section 3 in swollen condition, as shown, contacts the inner walls of tube 1 and covers a pair of opposing ports 2. The seal formed here is liquid tight, except for such liquid as may pass through the hydrogel material itself, and bacteria tight to reduce infection risk.

Figure 2:
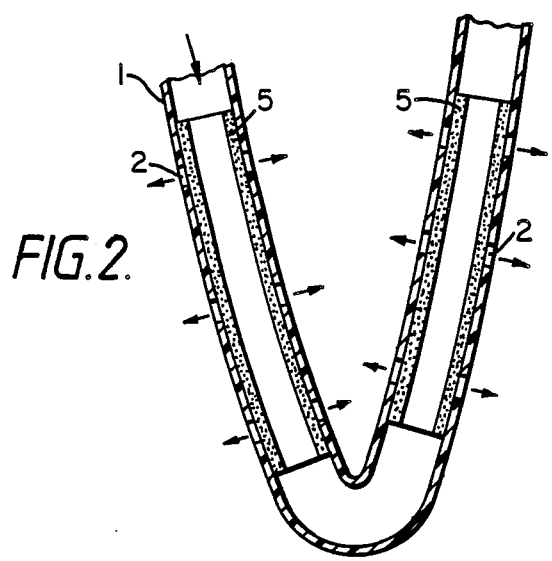
FIG. 2 is a section through another form of implant device according to the present invention.

FIG. 2 shows another form of implant device, wherein the device is of V, rather than U, shape. In addition in this device there is provided, on each arm of the V, only one annular cylinder 5 of hydrogel material within the tube 1. Thus in the embodiment of FIG. 2 the swollen hydrogel material 5 forms a substantially continuous layer of hydrogel along each arm of the device and covering all the ports 2 in that arm of the device.

Figure 4:
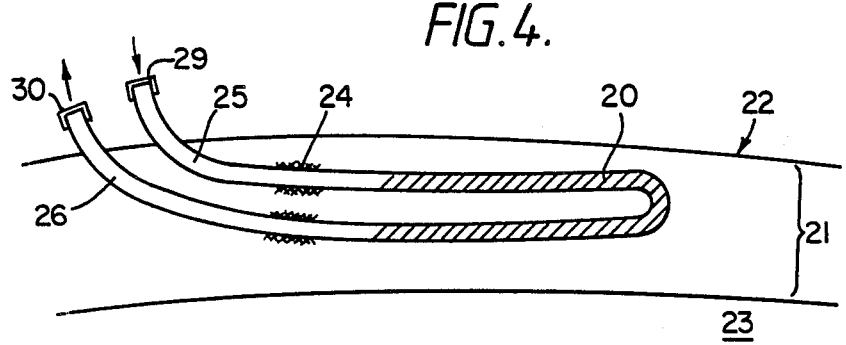
FIG. 4 illustrates the subcutaneous implantation of a device according to the present invention.
Figure 5:
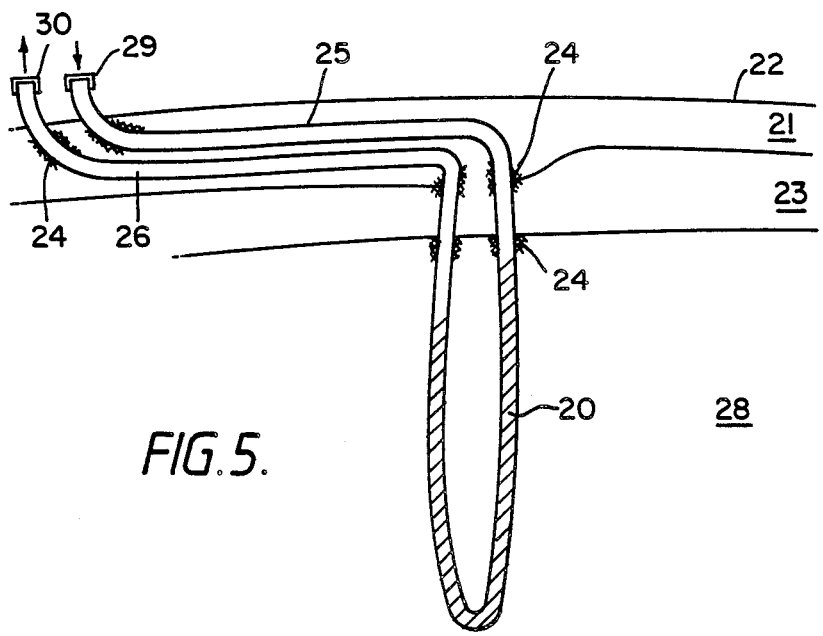
FIG. 5 illustrates the interperitoneal implantation of a device according to the present invention.

In use the device as illustrated in FIG. 1 or 2 is implanted surgically, e.g subcutaneously or interperitoneally, into the patient with the device according to the invention being connected to the outside of the patient as illustrated in FIG. 4 or 5 below. If the active substance to be used with the patient is to be non-aqueous, the hydrogel will be swollen before implantation. However if the active substance is to be used in aqueous solution this will be unnecessary. Thus the hydrogel material is hydrated and presses against the inside walls of tube 1 to provide liquid and bacteria tight seals across the ports 2 in the tube walls. Active substance introduced into the device according to FIG. 1 or FIG. 2 diffuses out through the hydrogel material of cylinders 3 and 5 across the ports 2 to be released into the patient.

Figure 3:
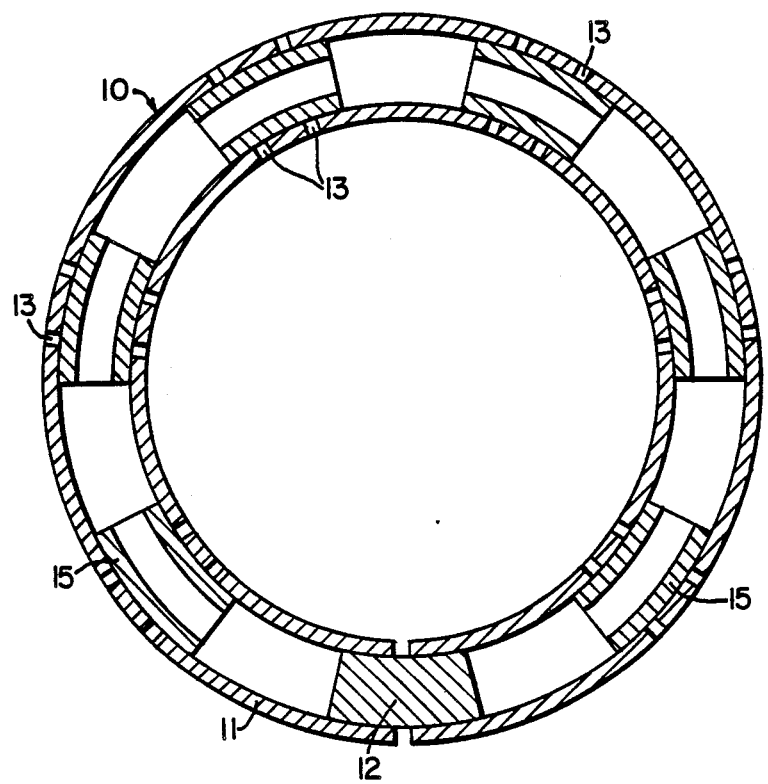
FIG. 3 is a section through a device according to the present invention for insertion into the vagina.

Referring to FIG. 3, there is shown a toroidal device 10 formed of a tube of elastomer material 11, constrained in the form of a toroid by means of the two ends of the tube 11 being held by means of a plug 12. There are a plurality of ports 13 in the wall of the tube 11. In addition, cylindrical sections 15 of hydrogel material are positioned inside the tube 11 such that, in the swollen state, these tubes of hydrogel material 11 press up against the inside of the tube 11 and extend across the ports 13. A, for example, contraceptive solution is provided within the toroidal device 10 and this ensures that the hydrogel sections 15 are maintained in the swollen state to seal the device.

In use the device of FIG. 3 is inserted into the patient's vagina around the cervix where contraceptive material will diffuse out through the hydrogel material 15 across the ports 13 to release contraceptive material in a sustained and controlled manner. When contraceptive material is exhausted from the device of FIG. 3, the device is removed from the vagina and either simply discarded and replaced by a new charged device or the device may be refilled by unplugging of plug 12, inserting new contraceptive solution and then replugging the device before replacing it in the vagina.

Alternatively, if the device of FIG. 3 is of self-sealing material, it may be implanted subcutaneously and used as a rechargeable implant.

Referring to FIG. 4, there is shown, diagrammatically, an implant device according to the present invention for example as shown in FIG. 1 or 2. This device 20 is positioned in the subcutaneous tissue 21 under the abdominal skin 22 and above the abdominal muscles 23. Stitching 24 provides anchorage of the device 20 to the tissue. Each end of the implanted device 20 is connected via tubes 25 and 26 respectively to the outside of the patient's body.

FIG. 5 illustrates the interperitoneal implantation of a device according to the present invention. The device 20 is inserted under the abdominal skin 22, subcutaneous tissue 21 and abdominal muscles 23 into the peritoneal cavity 28. As shown in FIG. 4, the device is anchored to the tissues by stitching 24. Also as shown in FIG. 4 each end of the device 20 is connected to the exterior of the patient via tubes 25 and 26 respectively. For interperitoneal implantation, these tubes 25 and 26 will generally be tunnelled under the abdominal skin 22.

Removable caps 29, 30 are provided on the external ends of the tubes 25, 26 respectively.

If desired the loop shape of the device according to the invention as shown in FIGS. 4 and 5 could be eliminated by securing the two opposing arms of the device 20 together.

In the treatment of for example a patient with thalassaemia active substance, desferrioxamine in isotonic aqueous solution, is introduced into the implanted device 20 along tube 25. Either the solution can be injected through cap 29 into tube 25 or the cap can be removed for introduction of the liquid. The solution travels along tube 25 into the device 20 from when the active substance diffuses through the hydrogel layers across the ports, into the surrounding body area. The rate of release of the desferrioxamine into the patient can be controlled by controlling the strength of the solution added, and the number and size of the ports and the nature and the thickness of the hydrogel of the device itself. When further active substance is required the device can be replenished by addition of further solution down tubing 25 into the device 20. When it is desired to remove, e.g. to clean out, the implanted device 20, this can be done by flushing through liquid down tubing 25 and out through tubing 26 to be discarded to the exterior.

The invention is also illustrated by way of example in the following Example

EXAMPLE

Hydrogel was prepared from the following:

| | |
|---|---|
| Poly(ethylene oxide), molecular weight 4360 | 1 mole |
| Poly(ethylene oxide), molecular weight 1610 | 0.5 mole |
| Poly(propylene oxide), molecular weight 445 | 1 mole |
| 1,2,6-hexane triol | 2 mole |
| Methylene-bis-(4-cyclohexyl isocyanate) | 5¼ mole |

The polymer was moulded into tubular sections of the following dimension:

| | Initial dry dimensions (mm) | Fully swollen dimensions (mm) |
|---|---|---|
| Inside diameter | 3.0 | 4.0 |
| Outside diameter | 6.0 | 8.0 |
| Wall thickness | 1.45 | 1.9 |
| Length | 20 | 27 |

The sections were placed into silicon tubing having a constant internal diameter of 3.8 mm and 11 mm external diameter having ports therethrough. Some of the tube lengths hold 60 ports each of 4 mm diameter i.e. a total port area of 7.5 cm . Other tube lengths had 60 ports each of 5 mm diameter giving a total port area of 11.8 $cm^2$.

Desferrioxamine solution (5 ml) was placed in the tubes as follows:

TABLE 1

| Run | Concentrate of desferrioxamine solution mg/ml | Port area $(cm)^2$ |
|---|---|---|
| A | 89 | 7.5 |
| B | 169 | 7.5 |
| C | 102 | 11.8 |
| D | 169 | 11.8 |

Each tube was sealed and immersed in 400 ml distilled water. The swollen hydrogel sections covered the ports in the tube.

The release rate of the desferrioxamine was as follows:

TABLE 2

| Time (hr) | Release rate (mg hr −1) | | | |
|---|---|---|---|---|
| | A | B | C | D |
| 20 | 3.1 | 6.4 | 5.1 | 6.75 |
| 40 | 2.8 | 4.2 | 3.5 | 4.8 |
| 60 | 2.3 | 3.6 | 2.8 | 3.6 |
| 80 | 1.7 | 3.1 | 2.3 | 2.9 |
| 100 | 1.2 | 2.7 | 2.0 | 2.55 |

We claim:

1. A sustained release device for releasing active substance from a cavity, when such cavity contains the active substance, through a layer of hydrogel extending across at least one port in a wall made of water-impermeable material, which device comprises:
   a container having a wall formed from a water-impermeable material, the wall having at least one port therethrough, and which wall defines the cavity for the reception of active substance; and
   within the container cavity, at least one body of hydrogel material, the hydrogel material, when in the dry state, being capable of being inserted into the container cavity and, when in the swollen condition, extending across the port or ports in the cavity wall and making sealing and pressing contact with the cavity wall adjacent the port or ports, said hydrogel material not being contiguous with the entire cavity wall.

2. The device according to claim 1 wherein the wall is of flexible material.

3. The device according to claim 1 wherein the hydrogel material when in swollen condition contacts the cavity wall substantially only in the region of the port or ports.

4. The device according to claim 1 which is in the form of a rechargeable surgical implant device and wherein the wall is of self-sealing material.

5. The device according to claim 1 which is in the form of a rechargeable surgical implant device and which is provided with at least one releasable seal whereby active substance can be introduced into the cavity when the device is implanted in a patient.

6. The device according to claim 1 which comprises a tube of water-impermeable material, the tube wall having a plurality of ports along its length, which tube contains one or more annular sections of hydrogel material which when in swollen condition covers the ports in the tube wall, the tube being sealed at its ends.

7. The device according to claim 1, wherein said water-impermeable material of said wall is medical grade silicon rubber.

8. The device according to claim 1, wherein said hydrogel is a material selected from the group consisting of crosslinked poly(ethylene glycol or ethylene oxide), polyacrylamides, poly-N-vinylpyrrolidones, polyhydroxyethyl and -propyl(meth)acrylates, polyoxyethylated derivatives of said (meth)acrylates, crosslinked polyvinyl alcohols, crosslinked starches, dextrans, polyhydric natural products, polyacrylic acids, polymethacrylic acids, crosslinked proteins and crosslinked glutamic acid.

9. A sustained release device for releasing active substance from a cavity containing the active substance, through a layer of hydrogel extending across at least one port in a wall made of water-impermeable material, which device comprises:
- a container having a wall formed from a water-impermeable material, the wall having at least one port therethrough, and which wall defines the cavity which contains said active substance; and
- within the container cavity, at least one body of hydrogel material, when in the dry state, being capable of being inserted into the container cavity and, when in the swollen condition, making sealing contact with the cavity wall adjacent the port or ports, said hydrogel material not being contiguous with the entire cavity wall.

10. The device according to claim 9 wherein the active substance is present in the device in saturated solution or is present in such amount that on introduction of aqueous medium into the device a saturated solution of the active substance is formed.

11. A method of administering active substance to a patient which method comprises implanting into or introducing into the patient's body a sustained release device for releasing active substance from a cavity containing the active substance through a layer of hydrogel covering at least one port in a wall made of water-impermeable material, wherein the wall defines the cavity and the cavity contains active substance and at least one body of hydrogel material which hydrogel material when in swollen condition is not contiguous with the entire cavity wall but covers the port or ports in the wall, and maintaining the hydrogel material in swollen condition, the active substance being released from the cavity through the hydrogel layer covering the port or ports into the patient's body.

12. A method of treating thalassaemia which method comprises implanting into or introducing into a patient's body a sustained release device for releasing active substance from a cavity containing the active substance through a layer of hydrogel covering at least one port in a wall made of water-impermeable material, wherein the wall defines the cavity and the cavity contains desferrioxamine in aqueous solution and at least one body of hydrogel material which hydrogel material when in swollen condition is not contiguous with the entire cavity wall but covers the port or ports in the wall, the desferrioxamine being released from the cavity through the hydrogel layer covering the port or ports into the patient's body.

13. The device according to claim 9, wherein said water-impermeable material of said wall is medical grade silicon rubber.

14. The device according to claim 9, wherein said hydrogel is a material selected from the group consisting of polyacrylamides, poly-N-vinylpyrrolidones, polyhydroxyethyl and -propyl(meth)acrylates, polyoxyethylated derivatives of said (meth)acrylates, crosslinked polyvinyl alcohols, crosslinked starches, dextrans, polyhydric natural products, polyacrylic acids, polymethacrylic acids, crosslinked proteins and crosslinked glutamic acid.

* * * * *